United States Patent
Dang et al.

(10) Patent No.: US 11,198,879 B2
(45) Date of Patent: Dec. 14, 2021

(54) MIXTURE OF CELL EXTRACT AND METHOD FOR SITE-DIRECTED CLONING

(71) Applicants: VIET NAM NATIONAL UNIVERSITY HO CHI MINH CITY, Ho Chi Minh (VN); Phuong Thao Thi Dang, Ho Chi Minh (VN); My Trinh Thi Nguyen, Hue (VN); Nghia Hieu Nguyen, Kien Giang (VN); Thuoc Linh Tran, Ho Chi Minh (VN)

(72) Inventors: Phuong Thao Thi Dang, Ho Chi Minh (VN); My Trinh Thi Nguyen, Hue (VN); Nghia Hieu Nguyen, Kien Giang (VN); Thuoc Linh Tran, Ho Chi Minh (VN)

(73) Assignee: VIET NAM NATIONAL UNIVERSITY HO CHI MINH CITY, Thu Duc (VN)

( * ) Notice: Subject to any disclaimer, the term of this patent is extended or adjusted under 35 U.S.C. 154(b) by 0 days.

(21) Appl. No.: 16/170,049

(22) Filed: Oct. 25, 2018

(65) Prior Publication Data
US 2020/0131521 A1    Apr. 30, 2020

(51) Int. Cl.
| | |
|---|---|
| C12N 15/66 | (2006.01) |
| C12N 15/90 | (2006.01) |
| C12N 1/06 | (2006.01) |
| C12N 1/20 | (2006.01) |
| C12N 1/16 | (2006.01) |
| C12R 1/19 | (2006.01) |
| C12R 1/865 | (2006.01) |
| C12N 1/18 | (2006.01) |

(52) U.S. Cl.
CPC ............ *C12N 15/66* (2013.01); *C12N 1/063* (2013.01); *C12N 1/16* (2013.01); *C12N 1/185* (2021.05); *C12N 1/20* (2013.01); *C12N 1/205* (2021.05); *C12N 15/90* (2013.01); *C12R 2001/19* (2021.05); *C12R 2001/865* (2021.05)

(58) Field of Classification Search
CPC .................................................. C12N 15/66
See application file for complete search history.

(56) References Cited

U.S. PATENT DOCUMENTS

| | | | | |
|---|---|---|---|---|
| 9,475,847 B2* | 10/2016 | Altier | ................ | A01N 63/10 |
| 2006/0110791 A1* | 5/2006 | Goyal | ................ | C12N 15/70 |
| | | | | 435/69.1 |
| 2007/0275920 A1* | 11/2007 | Muller | ................ | A61P 43/00 |
| | | | | 514/44 R |
| 2010/0167356 A1* | 7/2010 | Liu | ................ | C12N 15/66 |
| | | | | 435/91.2 |
| 2015/0241440 A1* | 8/2015 | Fasan | ................ | C12N 9/2442 |
| | | | | 506/18 |

OTHER PUBLICATIONS

Motohashi A simple and efficient seamless DNA cloning method using SLiCE from *Escherichia coli* laboratory strains and its application to SLiP site-directed mutagenesis 2015 BMC Biotechnology, 15:47; p. 1-9 (Year: 2015).*

Iizasa and Nagano. Highly efficient yeast-based in vivo DNA cloning of multiple DNA fragments and the simultaneous construction of yeast/*Escherichia coli* shuttle vectors2006. BioTechniques 40:79-83 (Year: 2006).*

Bose and Kumar. High-throughput clone screening followed by protein expression cross-check: A visual assay platform 2017 Analytical Biochemistry 516, 48-56 (Year: 2017).*

Novagen. pET-23a-d(+) Vectors 1998 Cat. No. 69745-3, TB051VM (Year: 1998).*

Hartley A.D., Santos M.A.S., Colthurst D.R., Tuite M.F. (1996) Preparation and Use of Yeast Cell-Free Translation Lysate. In: Evans I.H. (eds) Yeast Protocols. Methods in Molecular Biology™, vol. 53. Humana Press. https://doi.org/10.1385/0-89603-319-8: 249 (Year: 1996).*

Sambrook et al. Molecular Cloning: A Laboratory Manual (Third Edition), Cold Spring Harbor Press, 2001 (Year: 2001).*

UC Davis (2006. http://microbiology.ucdavis.edu/heyer/wordpress/wp-content/uploads/2013/11/YeastTransformation.pdf) (Year: 2006).*

EMBL (Extraction and Clarification—Preparation of cell lysates from yeast—Preparation of cell lysates from yeast using a French Press—EMBL; 2014). (Year: 2014).*

Invitrogen Cat. 18265-017 (Subcloning Efficiency™ DH5α™ Competent Cells 2006 Invitrogen Cat. 18265-017). (Year: 2006).*

* cited by examiner

*Primary Examiner* — Neil P Hammell
*Assistant Examiner* — Tiffany Nicole Grooms

(57) ABSTRACT

The present invention provides novel reagents and a cloning procedure based on homologous recombination for the site-directed cloning of a DNA fragment to a vector at designed site(s). The cloning reagents are made of mixture of extracts from at least two different cell types, preferably a mixture made of extracts from wild-type *E. coli* and *S. cerevisiae*. Due to the activity of the mixture of cell extracts, recombination occurs between the 3' and 5'-ends of the target DNA and at the ends of linearized vector, which facilitates in-frame construction of expression vectors.

20 Claims, 5 Drawing Sheets

MIXTURE OF CELL EXTRACT AND METHOD FOR SITE-DIRECTED CLONING

CROSS-REFERENCE TO RELATED APPLICATION

This application is based upon and claims priority to U.S. provisional patent application 62/707,368 entitled "Mixture of Cell Extract for Site-Directed Cloning" filed Oct. 31, 2017, the entire content of which is incorporated herein by reference.

FIELD OF THE INVENTION

The present invention relates generally to the field of DNA cloning. More specifically, the present invention relates to reagents and DNA cloning method based on homologous recombination for a site directed cloning of a DNA fragment into a vector.

BACKGROUND ART

Molecular cloning, or DNA cloning, refers to the process that inserts a DNA fragment into a vector such as plasmid, followed by the transformation into host cells in order to amplify a target DNA fragment or to express a recombinant protein. Since the first success in 1972, DNA cloning has been widely used and rapidly become the basic and critical technique in biology and biotechnology [1]. Due to its importance, a great number of methods has been developed by a multitude of laboratories to improve efficiency and to reduce the cost of cloning.

Restriction enzyme and ligase-dependent method are long considered as a traditional DNA cloning method. This method is involved two steps prior to the transformation process, which includes first using restriction enzymes to digest the DNA fragment of interest and the selected vector; and second, inserting the target DNA fragment into the linearized vector using a DNA ligase [2]. Although this method is simple, inexpensive, and flexible, it has some limitations due to the lack of appropriate restriction-sites, the difference in optimal conditions of restriction enzymes, and the high background of self-ligated vectors. Thus, this method tends to degrade the DNA cloning efficiency.

To improve the efficiency of DNA cloning, several ligase-independent methods and related kits have been developed and currently available on market such as Ligation Independent Cloning (LIC) developed by New England Biolabs (NEB), In-fusion kit developed by Takara, Cold-fusion kit developed by System Biosciences, etc. These methods are based on the presence of homologous sequences in the ends of the target DNA fragment and linearized vector through the activities of specific enzymes.

In the U.S. Pat. No. 7,575,860 entitled, "DNA Joining Method" to David Evans et al. (hereinafter referred to as the '860 Patent), a method for directionally cloning any linear template DNA molecule into any linearized vector is disclosed. In this method, DNA polymerases having exonuclease activity is used to efficiently join one or more linear DNA molecules sharing ends with appropriate complementation [3]. The method of the '860 Patent does not require the ligation step nor the use of carefully controlled conditions as is required in traditional cloning method.

In another U.S. Pat. No. 8,815,600 entitled, "Homologous Recombination Based DNA Cloning Methods and Compositions" to Liu et al. (hereinafter referred to as the '600 Patent'), methods and compositions for cloning a donor DNA molecule into an acceptor vector at a predetermined location are described [4]. The methods of the '600 patents are based on homologous recombination mediated by in vitro enzyme cocktail containing an exonuclease and a single-stranded DNA binding protein.

In general, these methods have advantages over the traditional method such as high cloning efficiency, the digestion of target fragment with restriction enzyme(s), and time-saving. However, because these techniques use purified enzymes, their cloning kits are expensive. Thus, small laboratories hesitate to use them.

In a patent application publication No. 2013/0045508 entitled, "Cell Extract Promoted Cloning" to Eldelmann et al. (herein after referred to as "'508 publication"), a method of assembling a plurality of double-stranded DNA fragments into DNA modules in a single in vitro recombination reaction is disclosed [6]. The chief aims of the method of the '508 publication are to insert a DNA fragment into a vector using cell extracts derived from a RecA-deficient *Escherichia coli* (hereinafter referred to as "*E. coli*") strain and requires homologous sequences in the ends of DNA molecules. There are three different mechanisms of homologous recombination in *E. coli*. The first is RecA-dependent, the second is RecA-independent, and the third is Red/ET-dependent [7]. RecA-dependent homologous recombination requires long homologous regions (150-300 bp), but it is the main and stronger recombination pathway. RecA-independent recombination pathway does not require long homologous sequence (a minimum of 12 bp) but it occurs at low efficiency in *E. coli* [8]. Therefore, although this method is easy, efficient, and cost-effective, the use of extract from *E. coli* cells lacking RecA, an important protein in bacterial repair system, might affect the recombination efficiency and induce mutations during cloning.

Furthermore, it is well known in the art that *E. coli* does not have tightly regulated DNA-repair mechanism in comparison to eukaryote cells. Therefore, unwanted mutations might occur during combination. On the other hand, in vivo DNA cloning based on yeast homologous recombination has been widely used due to its high efficiency [9]. The required homologous sequence is shorter, approximately 29 base pairs (bp) [10]. Additionally, the yeast recombination has strong mechanism for control of homologous DNA repair, which limits mutations [11]. However, there are no previous work that reportedly used the extracts of *Saccharomyces cerevisiae* (hereinafter referred to as "*S. cerevisiae*" or *Saccharomyces*") for in vitro DNA cloning. In fact, all intact *Saccharomyces* used in vivo cloning requires a vector that can replicate independently with yeast chromosome. This requirement limits the types of vectors that can be used.

Therefore, what is needed is a reagent for DNA cloning that is simple and cost-effective so that it can be used by small laboratories.

Furthermore, what is needed is a DNA cloning method that is easy to perform.

Yet, what is needed is a DNA cloning method that is accurate and efficient.

Yet, what is needed is a DNA cloning method that achieves minimal mutations. The present invention provides solutions to the above needs.

SUMMARY OF THE INVENTION

Accordingly, an objective of the present invention is to provide novel reagents and a cloning procedure based on homologous recombination for the site-directed cloning of a DNA fragment into a vector at designed site(s). The cloning reagents are made of mixture of extracts from at least two different cell types, preferably a mixture made of extracts from wild-type *E. coli* and *S. cerevisiae*. Due to the activity of the mixture of cell extracts, recombination occurs between the 3' and 5'-ends of the target DNA and at the appropriate ends of linearized vector, which facilitates in-frame construction of expression vectors.

Another objective of the present invention is to provide an efficient method of using reagents for DNA cloning that is cost-effective, simple to perform, and accurate with minimal mutations, especially for in-frame gene construction.

Yet another objective of the present invention is to provide a reagent in a DNA cloning procedure that will yield efficient and accurate results.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

It will be noted that the cloning efficiency mentioned herein refers to the ratio of colonies bearing the desired DNA fragment, which is inserted into vector in correct position, direction, and without mutation vs. the total number of colonies. The resulting vector from this cloning method might be used directly for expressing the target gene since correct site, proper direction assembly and no mutation are crucial for an efficient gene expression. Although we do not know the exact synergistic mechanism of the cell-extract mixture, it is clear that the yeast extract supported the function of *E. coli* proteins while controlling DNA repair processes that limit mutations.

As used herein, the term "wild-type *E. coli*" refers to the *E. coli* strain isolated from the natural environment and has not been genetically modified.

As used herein, the term yeast refers to the yeast *S. cerevisiae*. Accordingly, the wild-type yeast is the *S. cerevisiae* strain isolated from the natural environment and has not been genetically modified, whereas the term "laboratory strains" means the *S. cerevisiae* strains which has been genetically modified and widely used in laboratories.

As used herein, the term "polymerase chain reaction" (PCR) refers to a technique for rapidly synthesizing a huge amount of copies of a particular DNA fragment based on the activity of a DNA polymerase.

As used herein, the term "cDNA" indicates a DNA synthesized from a single stand mRNA through the action of an enzyme reverse transcriptase.

As used herein, the term "target DNA fragment" or "target fragment" refers to the DNA molecule which is inserted into a vector.

As used herein, the term "recombinant vector" means the vector containing the target DNA fragment.

Figure 1:
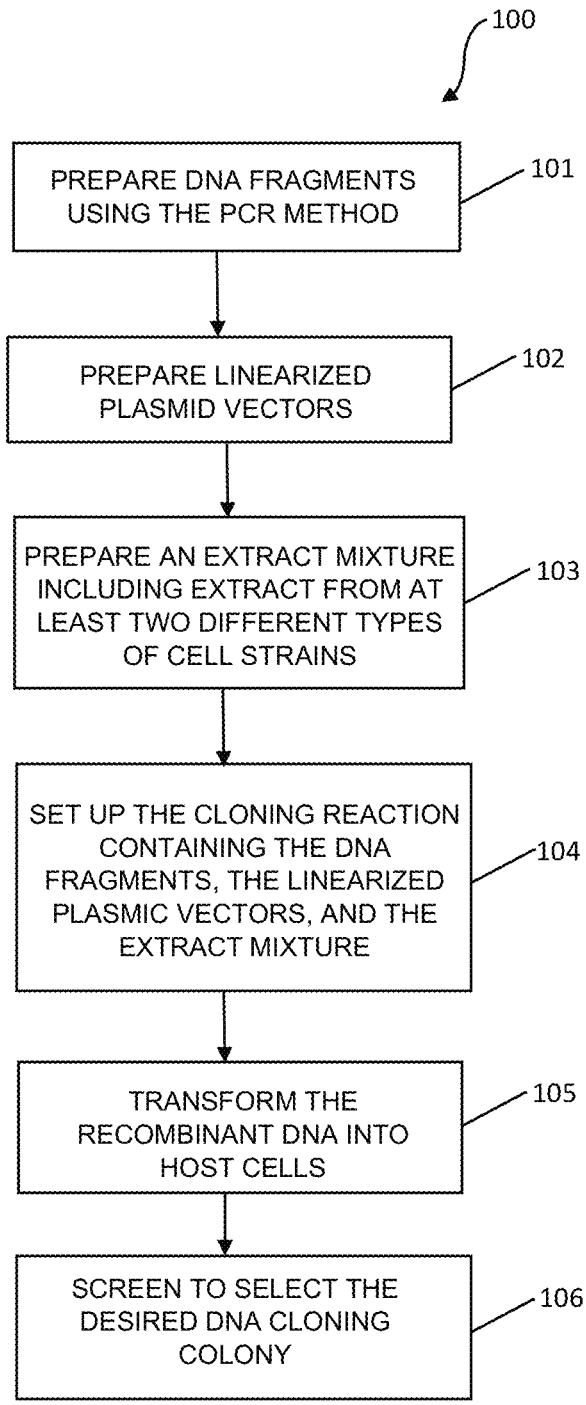
FIG. 1 is a flowchart of a DNA process that uses a reagent consisting extracts from *E. Coli* strains and *S. cerevisiae* strains in accordance with an embodiment of the present invention.

Many aspects of the present invention are now described with reference to FIG. 1-FIG. 3. FIG. 1 illustrates a flowchart of a method 100 of DNA cloning using a reagent including the extracts of *E. Coli* strains and *S. cerevisiae* strains in accordance with an embodiment of the present invention.

Method 100 begins at step 101 where DNA fragments are prepared. In one implementation of step 101 of the present invention, the DNA fragments can be produced by amplifying DNA or cDNA using a polymerase chain reaction (PCR) method. Each primer used in the PCR method contains two ends: a 5' end (or phosphate end) which is homologous to the appropriate end of the vector or another DNA fragment at the assembly site to allow the recombination, and a 3' end (or hydroxide) which is specific to the target fragment to ensures the successful PCR amplification.

Next at step 102, the plasmid vectors (or recipient cells) are linearized at the selected sites. In one implementation of step 102 of the present invention, the linearized vector can be generated either by digestion with restriction enzymes or by amplification of a circle vector using the PCR method.

At step 103, a reagent including extracts from *E. coli* strains and yeast strains are prepared. In one implementation of step 103 of the present invention, the *E. coli* strains are the wild-type *E. coli* strains. The wide-type strain was isolated from Laboratory of Molecular Biotechnology, VNU-HCM University of Sciences, Viet Nam and has been deposited with the Agricultural Research Service Culture Collection in Peoria, Ill., USA on Jun. 21, 2018 under the Budapest Treaty and was assigned accession number NRRL B-67662. The yeasts can be the wild-type or laboratory *S. cerevisiae* strains. The *S. cerevisiae* strains used in the implementation of step 103 are any commercial *S. cerevisiae* yeasts including, but not limited to, W303, BY4741, BY4742, MT8-1, and YPH250.

Continuing with step 103, in one aspect of the present invention, the *E. coli* strains having the identifying characteristics of deposit NRRL B-67662 are produced by the following specific steps:

(a) preparing a batch of wild-type *E. coli* strains overnight at 37° C. in a lubria broth (LB) medium to obtain a *E. coli* seed culture;

(b) diluting a 1 ml of the *E. coli* seed culture in a 100 ml fresh medium to obtain a diluted *E. coli* seed culture;

(c) culturing the diluted *E. coli* seed culture in step (b) above until an optical density measured at 600 nm wavelength ($OD_{600}$) value is 1.0 to obtain *E. coli* cells;

(d) centrifuging the *E. coli* cells in step (c) above at 5.000 rpm at 4° C. for 10 minutes and then washing them twice with distilled water ($dH_2O$) to collect a pellet of *E. coli* cells;

(e) suspending the pellet of *E. coli* cells in step (d) above in a buffer containing 1% SDS, 5 mM of an Ethylenediaminetetraacetic acid (EDTA);

(f) incubating the pellet of *E. coli* cells in step (e) above at room temperature for 10 minutes to lyse *E. coli* cells;

(g) removing the *E. coli* cell debris in step (f) above by a centrifugation at 13.000 rpm and 4° C. for 10 minutes to obtain a supernatant of *E. coli* cells;

(h) mixing the supernatant of the *E. coli* cells with an equal volume of 100% glycerol to obtain a mixture of *E. coli* extract; and (i) storing the mixture of *E. coli* extract at −30° C.

Continuing with step 103, any commercially available yeasts such as a W303, a BY4741, a BY4742, a MT8-1, and a YPH250 can be used with the above *E. coli* to generate the reagent of the present invention. In one exemplary implementation of step 103, a similar protocol with *E. coli* extract preparation was used to prepare the yeast extract. In brief, the *S. cerevisiae* W303 strain was grown overnight at 30° C. in a yeast peptone dextrose (YPD) medium to prepare the seed culture. More particularly, the *S. cerevisiae* W303 strain is prepared by the following process:

(h) growing a *S. cerevisiae* seed culture overnight at 30° C. in a yeast peptone dextrose (YPD) broth;

diluting a 1 ml of the *S. cerevisiae* W303 seed culture in a 100 ml of a fresh medium;

(j) culturing the *S. cerevisiae* seed culture in step (b) until an optical density measured at 60 nm wavelength ($OD_{600}$) value of 1.0 is achieved;

(k) collecting and washing the *S. cerevisiae* seed culture twice with distilled water ($dH_2O$) to obtain a pellet of *S. cerevisiae* cells;

(l) suspending and homogenizing the pellet of *S. cerevisiae* cells in step (d) in a 50 mM of Tris-HCl pH 7.0 to obtain a pellet of *S. cerevisiae* cells;

(m) removing debris from pellet of *S. cerevisiae* cells by a centrifugation process to obtain a supernatant of *S. cerevisiae* cells;

(n) mixing the supernatant of *S. cerevisiae* cells in step (f) with an equal volume of 100% glycerol to obtain a mixture of *S. cerevisiae* extract; and (o) storing the mixture of the *S. cerevisiae* extract at −30° C.

It will be appreciated that step 101, step 102, and step 103 are independent. That is, these steps can be performed in any order.

Next, at step 104, the cloning reaction is set up that includes the DNA fragments of step 101, the linearized plasmid vectors of step 102, and the reagent of step 103. In various implementations of step 104, the reaction mixture is allowed to react in vitro for a desired time at a desired temperature: the desired time ranges from 5 min to 2 days and the desired temperature ranges from room temperature to around 50° C. In a preferred implementation of step 104, the reaction conditions are 30 to 40° C. for 15-30 minutes when the length of each of the inserted DNA fragments is less than or equals to (≤) 1,000 base pairs (bp) and that of each of the DNA plasmid vectors is less than or equals to (≤) 7,500 bp. On the other hand, the reaction temperature is set at 37 to 45° C. for 30-60 minutes if the length of each of the DNA fragments is at least 1,000 bp and that of each of the DNA plasmid vectors is at least 7,500 bp.

Next at step 105, the recombinant DNAs obtained from step 104 are transformed into host cells. In various implementations of step 105, the recombinant DNA from the cloning reaction can be transformed into *E. coli* competent host cells using standard transformation methods in order to select and amplify recombinant vectors.

In one exemplary implementation, the recombinant DNA is introduced into the *E. coli* host cells if the lengths of the inserted DNA fragments and plasmid vectors are less than 2,000 base pairs (bp) and 10,000 bp respectively. As such, the *E. coli* host cells are cultured in an appropriate medium that can enable a quick screening process based on the resistance of antibiotics genes or α-complementation of the β-galactosidae genes following by the colony from PCR with specific primers. Finally at step 106, the result recombinant DNAs achieved from step 105 are screened to select the desired DNA cloning colony and store them at −30° C.

Figure 2:
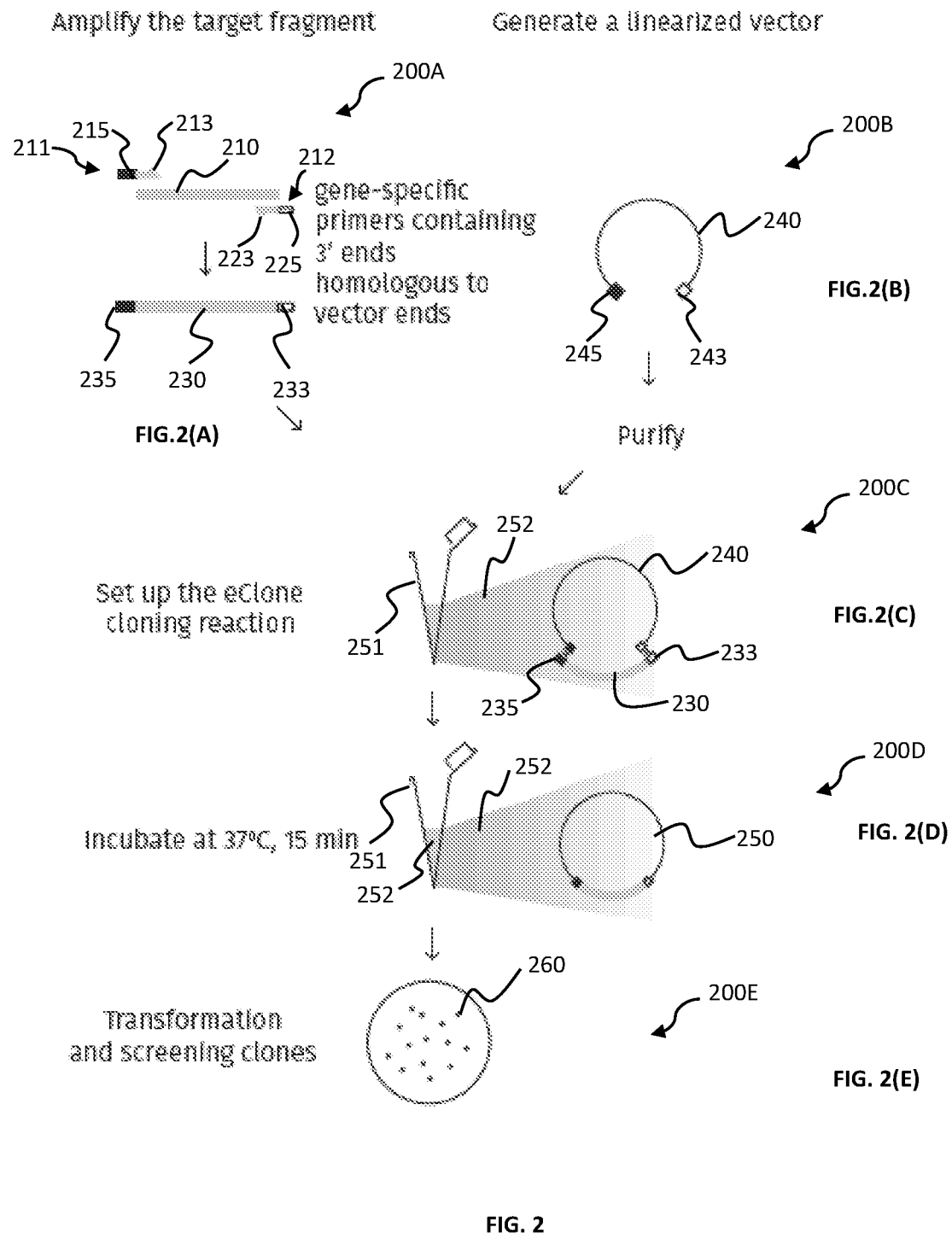
FIG. 2(A)-FIG. 2(E) are perspective diagrams 200A-200E illustrating the DNA cloning process using the reagent in accordance with an embodiment of the present invention.

Now referring to FIG. 2, perspective diagrams 200A-200E illustrating method 100 discussed in FIG. 1 is shown. In FIG. 2(A), a perspective diagram 200A illustrating a DNA fragment 230 is obtained from the target DNA template 210 using PCR method. A forward primer 211 and a reverse primer 212 are attached at both ends of DNA template 210 to start the exponential amplification of the template DNA. Forward primers 211 and reverse primer 212 for DNA amplification were designed as follows: (a) 5'-ends 215 and 225 containing 10, 15, or 20 nucleotides homologous to a respective 245 end and a 243 end of the vector/DNA fragment; and (b) 3'-ends 213, 223 containing 20 nucleotides specific to the target DNA fragment. Then both forward primer 211 and reverse primer 212 are extended by taq polymerase enzymes to achieve a DNA fragment (or segment or amplicon) 230 with 233 and 235 ends homologous to respective 243 end and 245 end of the plasmid vector 240. FIG. 2(A) and perspective diagram 200A illustrate step 101 above.

Next, in FIG. 2(B), a perspective diagram 200B illustrates step 102 in which a plasmid vector 240 having 245 and 243 ends is prepared. Plasmid vector 240 is then purified. FIG. 2(C) including a perspective diagram 200C, illustrates step 104 in which DNA cloning process 100 is performed in vitro in a laboratory environment using a container 251 where DNA fragment 230, plasmid vector 240, and a reagent 252—obtained as described in details at step 103 above—are allowed to react under specified time and temperature. In FIG. 2(D), a perspective diagram 200D shows that the cloning reaction is incubated at, for example, 37° C. for 30 minutes to allow the recombination of DNA fragment or amplicon 230 bearing the homologous 233 and 235 ends to combine with those of plasmid vector 240 to form a recombinant vector 250. Finally, FIG. 2(E) illustrates a perspective diagram 200E that implements step 106 described above. Perspective diagram 200E shows that colonies 260 of recombinant vector 250 are transformed into host cells and the screening process starts to achieve a competent colony of DNA clones.

Figure 3:
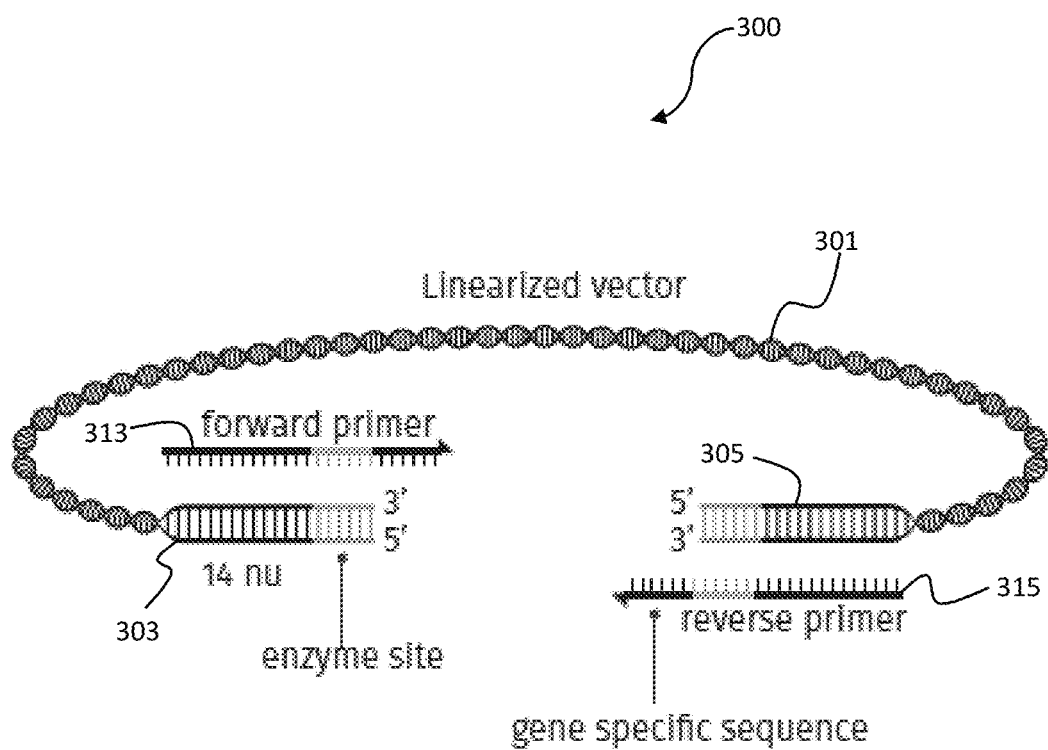
FIG. 3 is a perspective diagram 300 illustrating the design of a forward primer and a reverse primer in the amplification of a target DNA in accordance with an embodiment of the present invention.

Now referring to FIG. 3, a perspective diagram 300 illustrating the homologous recombination between a plasmid vector and an inserted DNA fragment is presented. Forward primers in DNA amplification 313 and reverse primers in DNA amplification 315 for DNA amplification are designed as follows: (a) 5'-end containing 10, 15, or 20 nucleotides homologous to the 303 and 305 ends of the vector 301; and (b) the 3'-end containing 20 nucleotides specific to the target DNA fragment. The backbone plasmid pET-28a(+) (Novagen) was used in all cloning experiments. For cloning one DNA fragment, the DNA fragments with different sizes were synthesized and named as ES1 (300 bp), ES2 (1000 bp), ES3 (1500 bp).

Figures 4A, 4B:
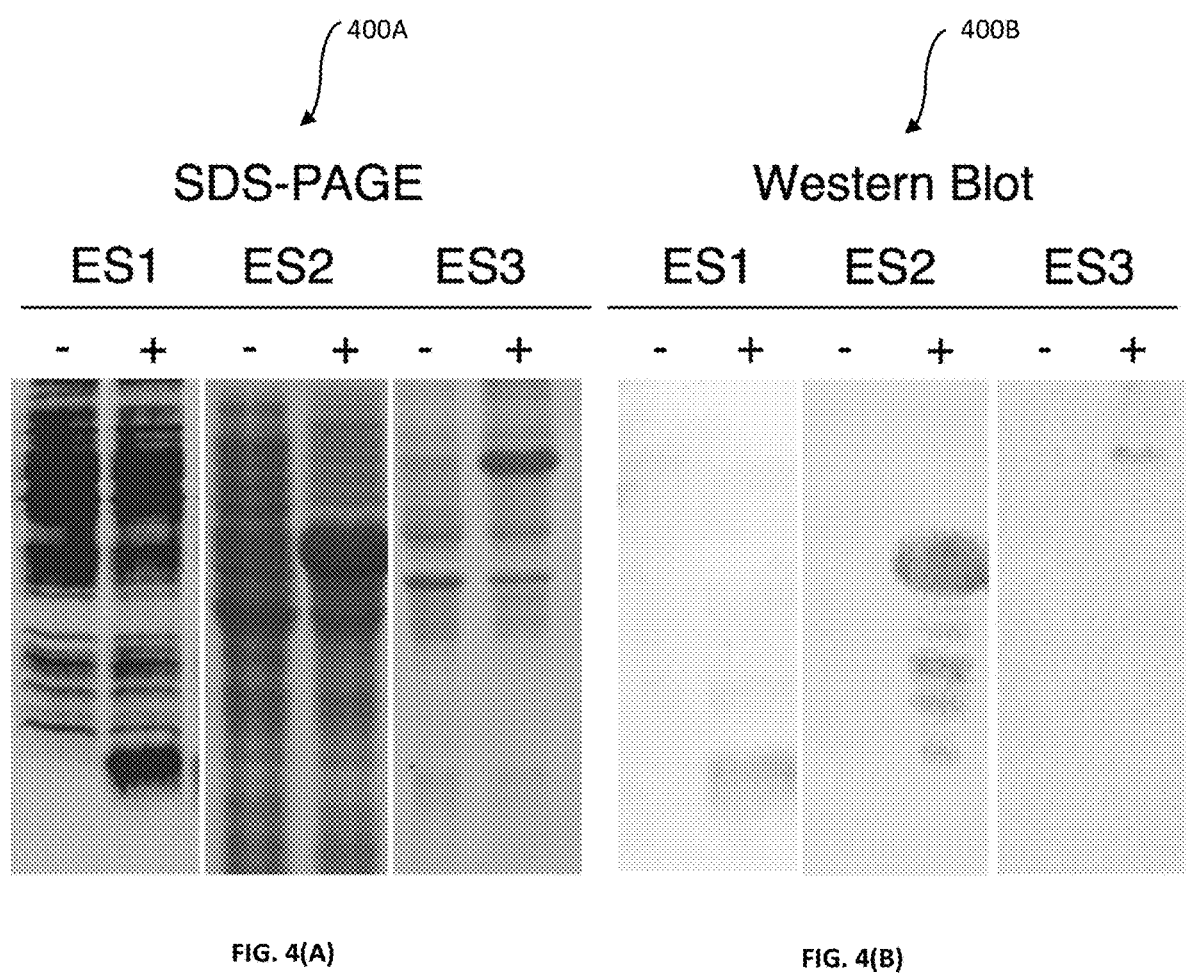
FIG. 4(A)-FIG. 4(B) illustrate SDS-PAGE 400A and Western Blot 400B of the results of the DNA cloning method of the present invention.

Now referring to FIG. 4, FIG. 4(A) shows the Sodium Dodecyl Sulfate Polyacrylamide Gel Electrophoresis (SDS-PAGE) graph FIG. 4(B) shows the Western Blot 400B illustrating the results verification of the expressions of ES1, ES2, and ES3 genes. More particularly, cells carrying recombinant 250 as obtained from step 106 are treated with 1 mM IPTG for 2 hours. The expression of protein was analyzed by SDS-PAGE technique where clear bands associated with different molecular weights are clearly shown in SDS-PAGE graph 400A of FIG. 4(A). On the other hand, the presence of target proteins ES1, ES2, and ES3 is detected by Western Blot analysis as shown in Western blot graph 400B of FIG. 4(B). Thus, it is indicated that method 100 of the present invention achieves the construction of plasmids for gene expression. Therefore, reagent 252 consisted of the mixture of extracts from *E. coli* strains and *S. cerevisiae* strains is suitable to construct expression plasmids.

Finally referring to FIG. 5(A) to FIG. 5(D), these figures illustrate the cloning efficiency of extract mixture at different time points during storage at 25° C. (room temperature) plotted in a graph 500A, 10° C. (refrigerator temperature) plotted a graph 500B, −30° C. (freeze temperature) plotted in a graph 500C, and −80° C. (deep freeze temperature) plotted in a graph 500D. The cloning efficiency is defined as the number of correct recombinant colonies obtained from each cloning experiment. To examine the changes in cloning efficiency of cell extract mixture during storage, the efficiency at the beginning is considered as 100%. Data are shown as mean±SD of three independent experiments.

Figure 5A:
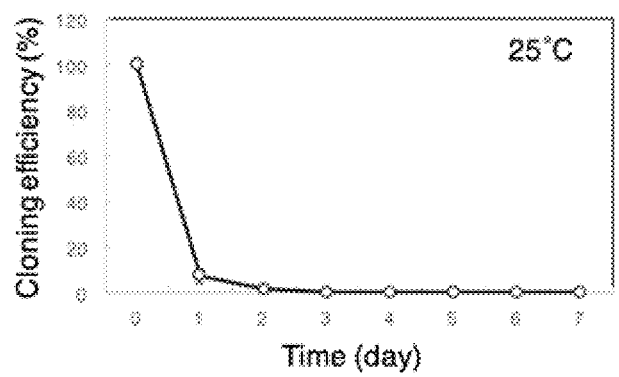
FIG. 5(A)-FIG. 5(D) show graphs 500A-500D illustrating the cloning efficiency of the extract mixture in different storage periods in accordance with the present invention.
Figure 5B:
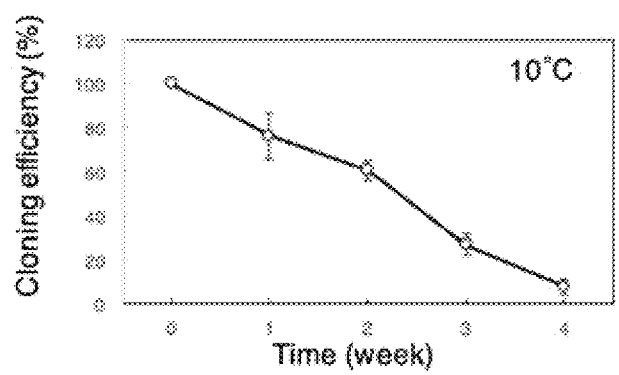
Figure 5C:
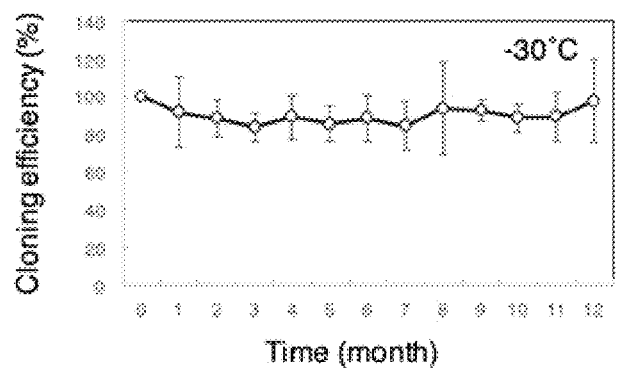
Figure 5D:
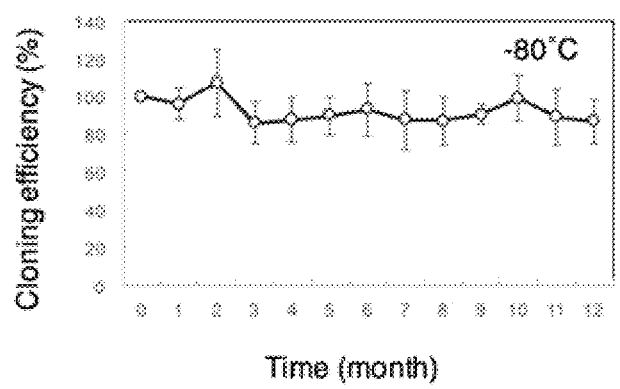

In FIG. 5(A), graph 500A shows that at 25° C., the activity of extract mixture rapidly decreases after the first day of storage. In FIG. 5(B), graph 500B shows that, at 10° C., the extract mixture gradually decreases during one month of storage. In contrast, in FIG. 5(C), graph 500C shows that the mixture can be retained at least 80% activity at −30° C. for one year. Finally, in FIG. 5(D), graph 500D shows that at −80° C. the mixture can also be retained for at least one year. Therefore, FIG. 5, graph 500A to graph 500D, suggests that storing the mixture below −30° C. for one year is the preferred condition.

In the present invention, the insertion one or several DNA molecule(s) into a vector at designed site(s) relies on enzymes provided by a mixture of cell extracts from selected *S. cerevisiae* and *E. coli* strains. The cell extract mixtures allow in vitro cloning with short homologous sequence length (~15 bp). Advantageously, the *E. coli* strains used in this invention is preferentially of wild type, contrarily to previously patented work that were limited to specialized RecA-deficiency bacteria strains. Prior to this invention, no one used RecA-dependent or wild type *E. coli* (which has RecA) cells for either in vivo or in vitro cloning methods.

This invention will be better understood from the Experimental Details and Results. However, one skilled in the art will readily appreciate that the specific methods and results discussed are merely illustrative of the invention as described more fully in the claims that follow thereafter.

Experimental Details and Results
  Materials and Methods
    Strains and Medium
    The *E. coli* strain used for extract preparation was isolated by Lab. Molecular Biotechnology, University of Science—Ho Chi Minh city. The *S. cerevsisiae* W303 strain was used to prepare the yeast extract. *E. coli* and *S. cerevisiae* cells were cultured in LB (10 g/L tryptone, 5 g/L yeast extract, and 10 g/L NaCl) and YPD (10 g/L yeast extract, 20 g/L peptone, and 20 g/L glucose) media, respectively.
    Plasmid, Insert fragments and Primers
    The backbone plasmid pET-28a(+) (Novagen) was used in all cloning experiments. For cloning one DNA fragment, the DNA fragments with different sizes were synthesized and named as ES1 (300 bp), ES2 (1000 bp), ES3 (1500 bp). Primers for DNA amplification were designed as following: the 5'-end containing 10, 15, or 20 nucleotides homologous to the appropriate end of the vector/DNA fragments it will join; and the 3'-end containing 20 nucleotides specific to the target DNA fragment. Please refer to FIG. 2(A)-FIG. 2(E) and respective diagrams 200A to 200E for more details.
    *E. coli* Extract Preparation
    The *E. coli* strain was grown overnight at 37° C. in LB medium to prepare the seed culture. Cells from 1 ml seed culture were diluted in 100 ml fresh medium and cultured further until they reached $OD_{600}$=1.0. Cells were collected by centrifugation at 5.000 rpm, 4° C. for 10 minutes and washed twice with $dH_2O$. The pellet was suspended in buffer containing 1% SDS, 5 mM EDTA (1 g cells in 10 ml buffer) and then incubated at room temperature for 10 minutes to lyse cells. Cell debris was removed by centrifugation at 13.000 rpm, 4° C. for 10 minutes. The supernatant was mixed with an equal volume of 100% glycerol and stored at −30° C.
    Yeast Extract Preparation
    A similar protocol with *E. coli* extract preparation was used to prepare the yeast extract. In brief, the *S. cerevisiae* W303 strain was grown overnight at 30° C. in YPD medium to prepare the seed culture. Cells from 1 ml seed culture were diluted in 100 ml fresh medium and cultured further until they reached $OD_{600}$=2.0. Cells were collected and washed twice with $dH_2O$. The pellet was suspended and homogenized in 50 mM Tris-HCl pH 7.0 (1 g cells in 10 ml buffer). Cell debris was removed by centrifugation and the supernatant was mixed with an equal volume of 100% glycerol and stored at −30° C.
    Cloning Protocol
    The vector was linearized using the restriction ezyme BamHI. DNA fragments were amplified using specific primers containing different length of homologous sequences at their 5' ends. A 15 µl reaction of 100 ng linearized plasmid, 30 ng DNA fragment, 1.5 µl buffer (50 mM Tris-HCl, 20 mM $MgCl_2$, 2 mM ATP, 20 mM DTT, pH 7.0 at 25° C.) and 1 µl extract mixture was prepared and incubated at 37° C. for 15 minutes to allow the homologous recombination. After that, 10 µl reaction mixture was transformed into 100 µl *E. coli* DH5α competent cells using classical calcium chloride ($CaCl_2$) method [12]. The transformed cells were plated on LB agar plates containing with 30 µg/L Kanamycin. Positive recombinant clones were selected by PCR with specific primers. The sequence accuracy of inserts was verified by DNA sequencing. All experiments were repeated at least 3 times.
    Expression Verification
    Several recombinant clones were randomly chosen and grown in 5 ml LB medium at 37° C. until they reached $OD_{600}$=0.5. After that, 1 mM isopropyl β-D-1-thiogalactopyranoside (IPTG) was added and cells were further cultured for 2 hours. Cells from 1 ml of each culture were collected by centrifuge, then suspended in 200 µl SDS-PAGE loading buffer (50 mM Tris-HCl, 2% SDS, 0.1% bromophenol blue, 10% glycerol, and 100 mM dithiothreitol) and incubated at 100° C. for 20 minutes. Ten microliter (µl) sample was applied to each lane of a 12.5% polyacrylamide gel for SDS-PAGE analysis. The 6×His-tagged proteins were detected by western blotting using a monoclonal anti-Histidine antibody (sc-8036, Santa Cruz biotechnology).

Combination of *E. coli* Extract and Yeast Extract Exerts a Synergic Effect on DNA Cloning It has been previously reported that *E. coli* extract has ability to assemble a linearized vector and a DNA fragment based on the presence of homologous sequences on them. In addition, an in vivo cloning method based on homologous recombination of intact yeast cells has been widely used due to its high efficiency and short homology requirement. These backgrounds prompted us to investigate whether the combination of *E. coli* extract and yeast extract shows a better effect on DNA cloning. Therefore, we performed cloning experiments using different combination ratios of these extracts to insert the ES2 fragment into the vector pET-28a (+). The homologous sequences containing 15 nucleotides was used in this experiment.

The *E. coli* extract but not the *S. cerevisiae* extract could work solely to combine the ES2 fragment and linearized pET-28a(+) (Table 2). Importantly, the mixture of 80% *E. coli* extract and 20% yeast extract (v/v) yielded the better efficiency, in which the number of transformed colonies and positive ratio were 38.0±6.2 and 96.7±5.8%, respectively. These data suggest that the combination of yeast extract and *E. coli* extract exerts the synergic effect on DNA cloning. However, the increase in yeast extract concentration in mixture gradually decreased the DNA cloning efficiency. This result might be explained by the dilution of *E. coli* extract components that negatively affects DNA cloning.

Due to the high efficiency, the combination 80% *E. coli* extract and 20% yeast extract was used in further experiments. See Table 1 below.

TABLE 1

Cloning efficiencies of different combination ratios of *E. coli* and yeast extracts

| Combination ratio (v/v) | | Number of colonies | Positive ratio* (% of obtained colonies) |
|---|---|---|---|
| *E. coli* extract | yeast extract | | |
| 100% | 0% | 111.3 ± 8.5 | 86.7 ± 5.8% |
| 80% | 20% | 189.0 ± 12.2 | 96.7 ± 5.8% |
| 60% | 40% | 127.7 ± 10.9 | 83.3 ± 15.3% |
| 40% | 60% | 34.7 ± 5.5 | 57.9 ± 8.4% |
| 20% | 80% | 6.0 ± 3.5 | 27.7 ± 25.4% |
| 0% | 100% | 0 | 1% |

*The positive colonies were selected by PCR with specific primers.

Effect of Homology Length on Cloning Efficiency

Since the frequency of homologous recombination is dependent on the homology length and insert size [13, 14], we next investigated the effect of these factors on the extract mixture-mediated cloning. Three genes with different sizes ES1, ES2, and ES3 were used in these experiments. Each gene was amplified by PCR using 3 primers pairs distinguished by the homology length at their 5'-ends. The results showed that the increase in insert sizes obstructed the DNA cloning whereas the increase in homology lengths improved cloning efficiency. Accordingly, the homologous sequence containing 10 nucleotides was sufficient for cloning of ES1 fragment whereas the longer homologous sequences, at least 15 nucleotides and 20 nucleotides, were required for efficient cloning of ES2 and ES3 fragments, respectively. See Table 2.

TABLE 2

Effect of insert size and homology length on cloning

| | Homology length | | |
|---|---|---|---|
| Insert name | 10 nucleotides | 15 nucleotides | 20 nucleotides |
| ES1 (300 bp) | 209.7 ± 17.7 (93.3 ± 8.9%) | 318.7 ± 31.0 (99.3 ± 0.6%) | 333.0 ± 39.3 (99.7 ± 0.6%) |
| ES2 (1000 bp) | 131.0 ± 13.3 (27.8 ± 5.2%) | 166 ± 14.3 (66.7 ± 4.4%) | 182.0 ± 19.3 (60.3 ± 6.9%) |
| ES3 (1500 bp) | 8.0 ± 2.9 (0%) | 108.0 ± 13.6 (45.6 ± 17.0%) | 144.3 ± 13.6 (44.5 ± 9.2%) |

DNA Sequencing Results Showed High Sequence Accuracy

To examine whether this cloning method induces mutations, 10 clones of each experiment were randomly chosen for DNA sequencing. The results showed that 100% clones contained correct insert sequences. See Table 3. This demonstrated that the extract mixture-mediated cloning is a highly accurate method.

TABLE 3

Percentage of plasmids bearing DNA insert with correct sequence.

| Insert name | Percentage of correct plasmids |
|---|---|
| ES1 (300 bp) | 100% |
| ES2 (1000 bp) | 100% |
| ES3 (1500 bp) | 100% |

The Extract Mixture-Mediated Cloning is a Site-Directed Method

In the next step, whether the target DNA can be inserted into the correct site in plasmid based on DNA sequencing data is determined. The results show that 100% recombinant plasmid bearing target DNA fragments at the proper positions and correct direction. See Table 4 below.

TABLE 4

Percentage of plasmids bearing DNA insert at proper sites

| Insert name | Percentage of plasmids bearing DNA insert at correct direction | Percentage of plasmids bearing DNA insert at proper site |
|---|---|---|
| ES1 (300 bp) | 100% | 100% |
| ES2 (1000 bp) | 100% | 100% |
| ES3 (1500 bp) | 100% | 100% |

The Extract Mixture-Mediated Cloning Method is Suitable to Construct Expression Plasmids All examined DNA fragments in this invention were designed and inserted into plasmid pET-28a(+) at EcoRV site and in-frame with 6×His-tag sequence so that they can be expressed under the control of T7 promoter. Therefore, in order to verify gene expression, several recombinant plasmids were randomly chosen and transformed into *E. coli* BL21(DE3). The presence of target proteins was detected by SDS-PAGE and Western Blot using anti-Histidine antibody since the proteins were fused with 6×His-tag. The representative SDS-PAGE and Western Blot results were shown in FIG. 4 and the quantitative data were shown in Table 5. In all samples from transformed BL21(DE3) clones, clear bands with defined molecular weights corresponding to the target proteins could be observed in both SDS-PAGE and Western Blot results, indicating that we succeeded in construction of plasmids for gene expression using this cloning method. Therefore, the extract mixture seems to be suitable to construct expression plasmids.

TABLE 5

Percentage of clones which could express the target protein

| Protein name | Percentage of expression clones |
|---|---|
| ES1 | 100% |
| ES2 | 100% |
| ES3 | 100% |

Examining the Stability of Extract Mixture Under Several Storage Conditions

For the purpose of product commercialization, the stability of extract mixture during storage at 25° C. (room temperature), 10° C. (refrigerator temperature), −30° C. (freeze temperature), and −80° C. (deep freeze temperature) was examined.

At 25° C., the activity of extract mixture rapidly decreased after the first day of storage is shown in graph 500A of FIG. 5A. At 10° C., the extract mixture gradually decreased during one month of storage is shown in graph 500B of FIG. 5B. In contrast, the mixture retained at least 80% activity at −30° C. and −80° C. for at least one year as shown in graph 500C of FIG. 5C and graph 500D of FIG. 5D respectively, which suggests that these conditions would be suitable for long storage of the mixture.

CONCLUSION

In the present invention, the extract from wild-type E. coli cells could allow the in vitro DNA assembly. More importantly, the combination of 80% wild-type E. coli extract and 20% yeast extract demonstrated a synergic effect on DNA cloning. Using the extract mixture, the cloning one or multiple DNA fragments up to 1500 bp long containing 10-20 bp homologous sequence into vector at proper sites and correct direction was successful. Since this cloning method is not depended on DNA ligase activity, the ratios of positive clones to all obtained clones are relatively high, that can speed up the subsequent screening and verification steps. In addition, as discussed above, unlike the previous related inventions that did not mention gene expression, the present invention showed that all tested recombinant clones could express target proteins, suggesting the improvement of the present method in constructing expression vectors. Therefore, the cell extract mixture of the present invention, which can be maintain its DNA assembly activity for at least one year at below −30° C., has a great potential for the development of an easy, cost-effective, accurate and site-directed DNA cloning kit that the market long awaits for but could not achieve.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

REFERENCES

1. Cohen, S. N., *DNA cloning: a personal view after 40 years*. Proc Natl Acad Sci USA, 2013. 110(39): p. 15521-9.
2. Griffiths, A. J. F., et al., *An Introduction to Genetic Analysis*. 7th edition. 2000, New York: W. H. Freeman.
3. Evans, D. H., D. O. Willer, and X.-D. Yao, *DNA joining method*. 2009, Google Patents.
4. Liu, W., et al., *Homologous recombination-based DNA cloning methods and compositions*. 2014, Google Patents.
5. Yu, H., *Homologous recombination-based nucleic acid molecular cloning method and related kit*. 2015, Google Patents.
6. Edelmann, W. and Y. Zhang, *Cell extract promoted cloning*. 2013, Google Patents.
7. Kowalczykowski, S. C., et al., *Biochemistry of homologous recombination in Escherichia coli*. Microbiological reviews, 1994. 58(3): p. 401-465.
8. Dutra, B. E., V. A. Sutera, and S. T. Lovett, *RecA-independent recombination is efficient but limited by exonucleases*. Proceedings of the National Academy of Sciences of the United States of America, 2007. 104(1): p. 216-221.
9. Finnigan, G. C. and J. Thorner, *Complex in vivo ligation using homologous recombination and high-efficiency plasmid rescue from Saccharomyces cerevisiae*. Bio-protocol, 2015. 5(13).
10. Ma, H., et al., *Plasmid construction by homologous recombination in yeast*. Gene, 1987. 58(2): p. 201-216.
11. Hua, S.-b., et al., *Minimum Length of Sequence Homology Required for in Vivo Cloning by Homologous Recombination in Yeast*. Plasmid, 1997. 38(2): p. 91-96.
12. Swords, W. E., *Chemical transformation of E. coli, in E. coli Plasmid Vectors*. 2003, Springer. p. 49-53.
13. Fujitani, Y., K. Yamamoto, and I. Kobayashi, *Dependence of frequency of homologous recombination on the homology length*. Genetics, 1995. 140(2): p. 797-809.
14. Kung, S. H., et al., *Effects of DNA size on transformation and recombination efficiencies in Xylella fastidiosa*. Applied and environmental microbiology, 2013. 79(5): p. 1712-1717.

DESCRIPTION OF NUMERALS

210 DNA template
211 forward primer
212 reverse primer
215 5'—end of forward primer
213 3'—end of forward primer
225 5'—end of reverse primer
223 3'—end of reverse primer
230 Amplicon or DNA fragment
235 one end of amplicon generated from 213 sequence through PCR
233 one end of amplicon generated from 215 sequence through PCR
240 plasmid vector
243 one end of the plasmid vector homologous to 233 sequence 245 one end of the plasmid vector homologous to 235 sequence
250 recombinant plasmid vector
251 in vitro container
252 Reagent consisting of *S. cerevisiae* and *E. coli* extracts
260 container for cell transformation and screening
301 linearized plasmid vector
303 one end of the linearized plasmid vector homologous to 5' end of forward primer
305 one end of the linearized plasmid vector homologous to 5' end of reverse primer
313 forward primer in DNA amplification
315 reverse primer in DNA amplification

What is claimed is:

1. A method of DNA cloning, comprising:
   (g) preparing DNA fragments by a polymerase chain reaction (PCR);
   (h) preparing plasmid vectors each having specific sequence elements and linearized at selected sites;
   (i) preparing a DNA cloning reagent consisting of a mixture of extracts from wild-type *E. coli* and yeast;
   (j) setting up a cloning reaction between said DNA fragments, said plasmid vectors, said DNA cloning reagent, and a buffer to obtain a mixture of recombinant DNA;
   (k) transforming said mixture of recombinant DNA into host *E. coli* cells different from said wild-type *E. coli* in said mixture of said step (c); and
   (l) screening and verifying to select a DNA cloning batch that includes said DNA fragments generated by said PCR.

2. The method of claim 1 wherein said DNA fragments are characterized by specific sequence elements at both ends which are exactly the same as those of a DNA vector at said selected sites, wherein said DNA fragments are amplicons from said polymerase chain reaction (PCR) that use primers that contain said specific sequence elements at phosphate (5') ends and at hydroxide (3') ends.

3. The method according to claim 2, wherein said setting up a cloning reaction of step (d) further comprises: maintaining said cloning reaction between 15-30 minutes at a temperature between 30° C. to 40° C. if said length of DNA fragments is less than or equals to 1,000 base pairs (bp) and said length of said plasmid vector is less than or equals to 7,500 bp; and
   maintaining said cloning reaction between 30-60 minutes at a temperature 40° C. if said length of said DNA fragments is at least 1,000 base pairs (bp) and length of said plasmid vector is at least 7,500 bp.

4. The method according to claim 2, wherein said transforming said recombinant DNA into said *E. coli* cells as hosts of step (e) comprises using a heat shock.

5. The method according to claim 2 wherein said DNA fragments comprises 300 base pairs and said specific sequence elements contain 10 nucleotides.

6. The method according to claim 2 wherein said DNA fragments comprises 300 base pairs and said specific sequence elements contain 15 nucleotides.

7. The method according to claim 2 wherein said DNA fragments comprises 300 base pairs and said specific sequence elements contain 20 nucleotides.

8. The method according to claim 2, said DNA fragments comprises 1,000 base pairs and said specific sequence elements contain 10 nucleotides.

9. The method according to claim 2, wherein said DNA fragments comprises 1,000 base pairs and said specific sequence elements contain 15 nucleotides.

10. The method of claim 2 wherein said DNA fragments comprises 1,000 base pairs and said specific sequence elements contain 20 nucleotides.

11. The method according to claim 2 wherein said DNA fragments comprises 1,500 base pairs and said specific sequence elements contain 10 nucleotides.

12. The method according to claim 2, wherein said transforming said recombinant DNA into said *E. coli* cells as hosts of step (e) comprises using an electroporation.

13. The method according to claim 2 wherein said DNA fragments comprises 1,500 base pairs and said specific sequence elements contain 15 nucleotides.

14. The method according to claim 2 wherein said DNA fragments comprises 1,500 base pairs and said specific sequence elements contain 20 nucleotides.

15. The method of claim 2 wherein said specific sequence elements further comprise at least 15 base pairs (bp) which are synthesized based on a nucleotide sequence at said selected sites of said DNA vector.

16. The method of claim 1 wherein said buffer is composed of a Tris-HCl at 50 mM concentration, a Magnesium chloride ($MgCl_2$) at 20 mM concentration, an adenosine triphosphate (ATP) at 2 mM concentration, and a Dithiothreitol (DTT) at 20 mM concentration, all at a pH level of 7.0 and at 25° Celsius.

17. The method according to claim 1, wherein said yeast is *S. cerevisiae* and said mixture of extracts from wild-type *E. coli* and yeast having a combination ratio of 80% of wild-type *E. coli* and 20% of *S. cerevisiae* yeast.

18. The method of claim 17 wherein said extract of *S. cerevisiae* is produced from a method comprising the steps of:
   preparing a *S. cerevisiae* seed culture by growing a *S. cerevisiae* strain overnight at 30° C. in a yeast extract-Peptone-Dextrose (YDP) medium;
   diluting 1 ml of said *S. cerevisiae* seed culture in 100 ml of fresh medium;
   culturing said *S. cerevisiae* seed culture until an optical density measured at 60 nm wavelength ($OD_{600}$) value of 1.0 is achieved;
   centrifuging said *S. cerevisiae* culture at 5,000 rpm at 4° C. for 10 minutes to collect a pellet of *S. cerevisiae* cells;
   washing said pellet of *S. cerevisiae* cells by adding distilled water ($dH_2O$) into said pellet of *S. cerevisiae* cells, suspending said pellet of *S. cerevisiae* cells, and then centrifuging said suspended *S. cerevisiae* cells to collect a washed pellet of *S. cerevisiae* cells;
   re-suspending and homogenizing said washed pellet of *S. cerevisiae* cells in 50 mM Tris-HCL pH 7.0 to obtain *S. cerevisiae* lysates;
   removing debris of said *S. cerevisiae* lysates by a centrifugation process to obtain a supernatant of *S. cerevisiae* lysates;
   mixing said supernatant of *S. cerevisiae* lysates with an equal volume of 100% glycerol to obtain a mixture of said extract of *S. cerevisiae*; and
   storing said mixture of said extract of *S. cerevisiae* at −30° C.

19. The method of claim 1 wherein said mixture extracts from wild-type *E. coli* from said DNA cloning reagent are produced from a process comprising:

preparing a batch of wild-type *E. coli* strains overnight at 37° C. in a Luria-Bertani (LB) medium to obtain a wild-type *E. coli* seed culture;

diluting 1 ml of said wild-type *E. coli* seed culture in 100 ml fresh medium to obtain a diluted wild-type *E. coli* seed culture;

culturing said diluted wild-type *E. coli* seed culture until an optical density measured at 60 nm wavelength ($OD_{600}$) value is 1.0 to obtain wild-type *E. coli* cells;

centrifuging said wild-type *E. coli* cells at 5,000 rpm at 4° C. for 10 minutes and then washing said wild-type *E. coli* cells twice with distilled water ($dH_2O$) to collect a pellet of wild-type *E. coli* cells;

re-suspending said pellet of wild-type *E. coli* cells in a buffer containing 1% SDS, 5 mM Ethylenediaminetetraacetic acid (EDTA);

incubating said pellet of wild-type *E. coli* cells at room temperature for 10 minutes to lyse said wild-type *E. coli* cells; and removing said wild-type *E. coli* cell debris by a centrifugation at 13,000 rpm and 4° C. for 10 minutes to obtain a supernatant of wild-type *E. coli* cells;

mixing said supernatant of said wild-type *E. coli* cells with an equal volume of 100% glycerol to obtain a mixture of said extracts from wild-type *E. coli*; and storing said mixture of said extracts from wild-type *E. coli* at −30° C.

20. A method of DNA cloning comprising a reaction between a DNA cloning reagent consisting of mixture extracts of wild-type *E. coli* and *S. cerevisiae* yeast and a plurality of DNA fragments.

\* \* \* \* \*